(12) United States Patent
Hiramoto et al.

(10) Patent No.: US 7,589,334 B2
(45) Date of Patent: Sep. 15, 2009

(54) ION BEAM DELIVERY EQUIPMENT AND AN ION BEAM DELIVERY METHOD

(75) Inventors: Kazuo Hiramoto, Hitachiohta (JP);
Hiroshi Akiyama, Hitachiohta (JP);
Masaki Yanagisawa, Hitachi (JP);
Hisataka Fujimaki, Hitachinaka (JP);
Alfred Smith, Houston, TX (US);
Wayne Newhauser, Houston, TX (US)

(73) Assignees: Hitachi, Ltd., Tokyo (JP); Board of Regents, University of Texas System, Austin, TX (US)

( * ) Notice: Subject to any disclaimer, the term of this patent is extended or adjusted under 35 U.S.C. 154(b) by 52 days.

(21) Appl. No.: 11/714,219

(22) Filed: Mar. 6, 2007

(65) Prior Publication Data

US 2007/0158592 A1 Jul. 12, 2007

Related U.S. Application Data

(63) Continuation of application No. 11/039,960, filed on Jan. 24, 2005, now abandoned.

(51) Int. Cl.
*G21G 5/00* (2006.01)
(52) U.S. Cl. .................. 250/492.21; 250/492.3; 250/492.22; 250/493.1; 250/492.1
(58) Field of Classification Search ............. None
See application file for complete search history.

(56) References Cited

U.S. PATENT DOCUMENTS

| 4,794,340 | A | 12/1988 | Ogasawara |
| 5,363,008 | A | 11/1994 | Hiramoto et al. |
| 7,449,701 | B2 | 11/2008 | Fujimaki et al. |
| 2007/0158592 | A1 | 7/2007 | Hiramoto et al. |

OTHER PUBLICATIONS

"Reviewing of Scientific Instruments" vol. 64, No. 8, pp. 2074-2084.
Kooy et al., "Monitor Unit Calculations for Range-Modulated Spread-Out Bragg Peak Fields" Phys. Med. Biol. 48 (2003) pp. 2797-2808.

*Primary Examiner*—David A. Vanore
(74) *Attorney, Agent, or Firm*—Dickstein Shapiro LLP

(57) ABSTRACT

The invention is intended to increase the number of patients treatable using one wheel having a thickness varied in the rotating direction to change energy of an ion beam passing the wheel. Ion beam delivery equipment for irradiating an ion beam to a patient for treatment comprises a beam generator for producing and accelerating the ion beam, an beam delivery nozzle including a range modulation wheel which has a predetermined thickness distribution in the rotating direction and is rotated on a travel passage of the ion beam generated from the beam generator to control a range of the ion beam, and an irradiation controller for controlling the beam producing and accelerating operation of the beam generator in accordance with the phase of rotation of the range modulation wheel.

15 Claims, 9 Drawing Sheets

US 7,589,334 B2

ION BEAM DELIVERY EQUIPMENT AND AN ION BEAM DELIVERY METHOD

CROSS REFERENCE TO RELATED APPLICATIONS

This application is a continuation of U.S. patent application Ser. No. 11/039,960, filed on Jan. 24, 2005, now abandoned the entire disclosure of which is hereby incorporated by reference herein.

BACKGROUND OF THE INVENTION

1. Field of the Invention

The present invention relates to ion beam delivery equipment and ion beam delivery method, which are used to produce and deliver ion beam, e.g., proton or carbon ions, to a tumor for treatment.

2. Description of the Related Art

There is known a method for delivering ion beam, e.g., proton or carbon ions, to a tumor, such as a cancer, in the body of a patient. The ion beam delivery equipment for such treatment comprises an ion beam generator to produce the said ion beam and accelerate it to a needed energy, a beam transport system, and an beam delivery nozzle. An ion beam accelerated by the beam generator reaches the beam delivery nozzle, which is installed in a rotating gantry to monitor and shape the therapeutic radiation field, through a first beam transport system and a second ion beam transport system, the latter being installed in the rotating gantry. The ion beam reached the beam delivery nozzle is delivered to the tumor in the patient body from the beam delivery nozzle. Known examples of the beam generator include a synchrotron (quasi-circular accelerator) provided with an extraction deflector for extracting the ion beam from the orbit (see, e.g., Patent Reference 1; U.S. Pat. No. 5,363,008).

In radiation therapy using an ion beam, e.g., with a proton beam delivering a radiation dosage to a tumor, by utilizing characteristics that most of the energy of the proton beam is released just before protons come to rest, namely that a Bragg peak is formed just before the stop of protons, the energy of the proton beam is selected to stop protons in the tumor so that the beam energy is released most to cells within the tumor or its microscopic extensions.

Usually, the tumor has a certain thickness in the direction of depth, i.e. along the direction of the ion beam, from the body surface of a patient (hereinafter referred to simply as "the direction of depth"). To effectively irradiate the ion beam over the entire thickness of the tumor in the direction of depth, the width of the Bragg peak must be spread out in the direction of depth. The spread-out width of the Bragg peak is called a Bragg peak width. To obtain the required Bragg peak width, the energy of the ion beam must be modulated.

From that point of view, a range modulation wheel (RMW) has already been proposed in which a plurality of blades each having a thickness varied step by step in the circumferential direction are installed around a rotating shaft (see, e.g., Non-patent Reference 1; "REVIEW OF SCIENTIFIC INSTRUMENTS", Vol. 64, No. 8, pp 2074-2084 (FIGS. 30 and 31) issued in August, 1993). The plural blades are mounted to the rotating shaft. In the RMW, a through opening is formed between adjacent sets of the blades. For example, when the RMW is rotated from a state in which the opening is positioned on a path of the ion beam (hereinafter referred to simply as a "beam path"), the opening and the blade alternately intersect the beam path. At the time when the ion beam passes through the opening, the energy of the ion beam is not attenuated and therefore the Bragg peak is produced in the deepest position inside the patient body. At the time when the ion beam passes through a blade, the energy of the ion beam is attenuated more as the ion beam passes through the blade having a larger thickness, and therefore the Bragg peak is produced in a portion of the tumor near the body surface of the patient. With the rotation of the RMW, the position in the direction of depth where the Bragg peak is formed varies cyclically. As a result, the Bragg peak width being comparatively wide and flat in the direction of depth of the tumor can be obtained, looking at the beam energy integrated over time.

SUMMARY OF THE INVENTION

The known method described above has the problem as follows.

Patients have body dimensions different from one another and tumor sizes also differ from one another. Accordingly, the Bragg peak width optimum for treatment of the tumor differs for each of the patients. With the known method, however, only one set Bragg peak width is obtained from one RMW. This has invited the necessity of forming and preparing a different RMW for each patient and replacing the RMW whenever the patient is changed, and hence has caused a difficulty in efficiently treating a large number of patients.

It is an objective of the present invention to provide an ion beam delivery equipment and an ion beam delivery method, which can increase the number of patients treatable using one wheel having a thickness varied in the rotating direction to change energy of the ion beam passing the wheel.

To achieve the above objective, the present invention is featured in that start and stop of extraction of the ion beam accelerated in the beam generator is controlled during rotation of a wheel having a thickness varied in the rotating direction to change energy of the ion beam passing the wheel. By controlling the start and stop of extraction of the ion beam from the beam generator during the rotation of the wheel, a region of the wheel where the ion beam passes the wheel can be changed in the rotating direction. It is therefore possible to form a plurality of spread-out beam peak (Bragg peak) widths (hereinafter referred to as "SOBP widths") having different values in the direction of depth from the body surface of a patient by using one modulation wheel, and to employ one wheel for a plurality of patients. In other words, various patients having tumors with different thickness can be treated with one modulation wheel.

Preferably, a synchrotron is used as the beam generator.

Preferably, the wheel is provided with a plurality of blades each having a thickness varied in the rotating direction.

Preferably, the control of the start and stop of extraction of the ion beam from the beam generator is done by using the information for the SOBP width sent from the treatment planning software through communication network.

According to the present invention, since the modulation wheel has the thickness varied in the rotating direction to change energy of the ion beam passing the wheel, the number of patients treatable using one modulation wheel can be increased.

DESCRIPTION OF THE PREFERRED EMBODIMENTS

Embodiments of the present invention will be described in detail below with reference to the drawings.

First Embodiment

Figure 1:
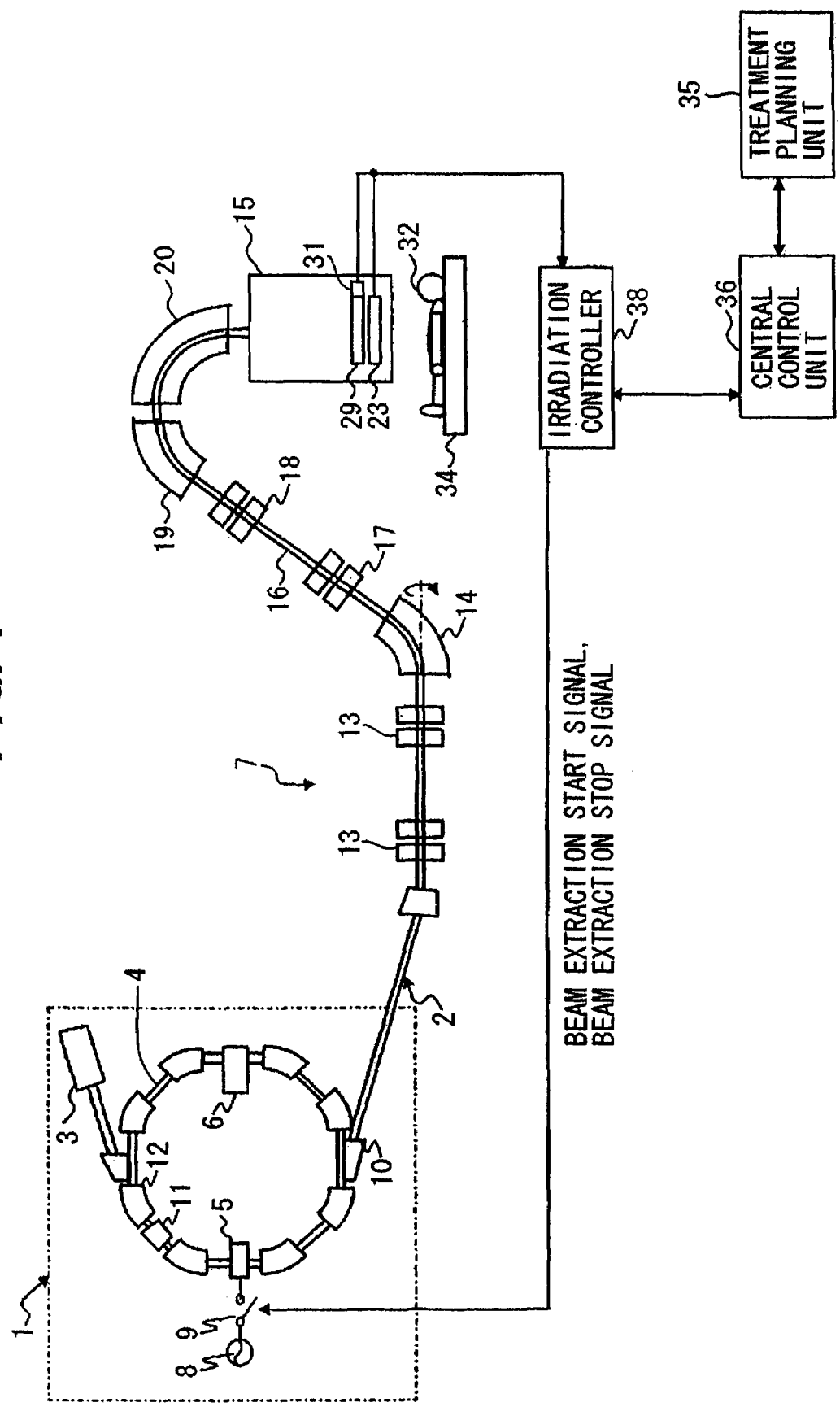
FIG. 1 is an overall block diagram of ion beam delivery equipment according to a first embodiment, i.e., one preferable embodiment, of the present invention.

Proton beam delivery equipment 7 as ion beam delivery equipment of this embodiment comprises, as shown in FIG. 1, a beam generator 1, a beam transport system 2, and an beam delivery nozzle 15, the latter two being connected downstream of the beam generator 1.

The beam generator 1 comprises an ion (proton) source (not shown), a pre-accelerator 3, and a synchrotron 4 serving as a main accelerator. The synchrotron 4 includes an RF-applying device 5 having a pair of electrodes and an RF-accelerating cavity 6. The RF-applying device 5 and the RF-accelerating cavity 6 are installed on an orbit of a circulating ion beam. A first RF-power supply 8 is connected to the electrodes of the RF-applying device 5 through an on/off switch 9. A second RF-power supply (not shown) for applying an RF power to the RF-accelerating cavity 6 is separately provided. Ions (e.g., proton ions (or carbon ions)) generated by the ion source are accelerated by the pre-accelerator 3 (e.g., a linear accelerator). An ion beam emitted from the pre-accelerator 3 enters the synchrotron 4. The ion beam (corpuscular beam) is accelerated by an electromagnetic field generated in the RF-accelerating cavity 6 with application of the RF power supplied from the second RF-power supply. The ion beam circulating in the synchrotron 4 is extracted from the synchrotron 4 upon closing of the on/off switch 9, as described later, after energy of the ion beam has been increased up to a setting level (e.g., 70 to 250 MeV). More specifically, an RF power is applied to the circulating ion beam from the first RF-power supply 8 through the RF-applying device 5 when the on/off switch 9 is closed. With the application of the RF power, the ion beam circulating within a stability limit is forced to exceed the stability limit and extracted from the synchrotron 4 through a beam extraction deflector 10. At the time of extracting the ion beam, currents supplied to quadrupole magnets 11 and bending magnets 12 both installed in the synchrotron 4 are held at setting current values, and hence the stability limit of the circulation is also held substantially constant. The extraction of the ion beam from the synchrotron 4 is stopped by opening the on/off switch 9 to stop the application of the RF power to the RF-applying device 5.

The ion beam extracted from the synchrotron 4 is transported to a downstream of the beam transport system 2. The beam transport system 2 includes quadrupole magnets 13 and a bending magnet 14, and the beam duct 16 connected to the beam delivery nozzle 15. The beam delivery nozzle 15 and the beam duct 16 are both mounted to a rotating gantry (not shown) installed in a treatment room (not shown). A quadrupole magnet 17, a quadrupole magnet 18, a bending magnet 19, and a bending magnet 20 are installed along the beam duct 16 in this order. The ion beam is transported along the beam duct 16 to the beam delivery nozzle 15 by these magnets. A patient 32 lies on a treatment couch 34 properly positioned in a treatment cage (not shown) that is formed within the rotating gantry. The ion beam emitted from the beam delivery nozzle 15 is delivered to a tumor, such as a cancer, in the body of the patient 32. The beam duct 16 with magnets, such as the quadrupole magnet 17, can also be regarded as a beam transport system.

Figure 2:
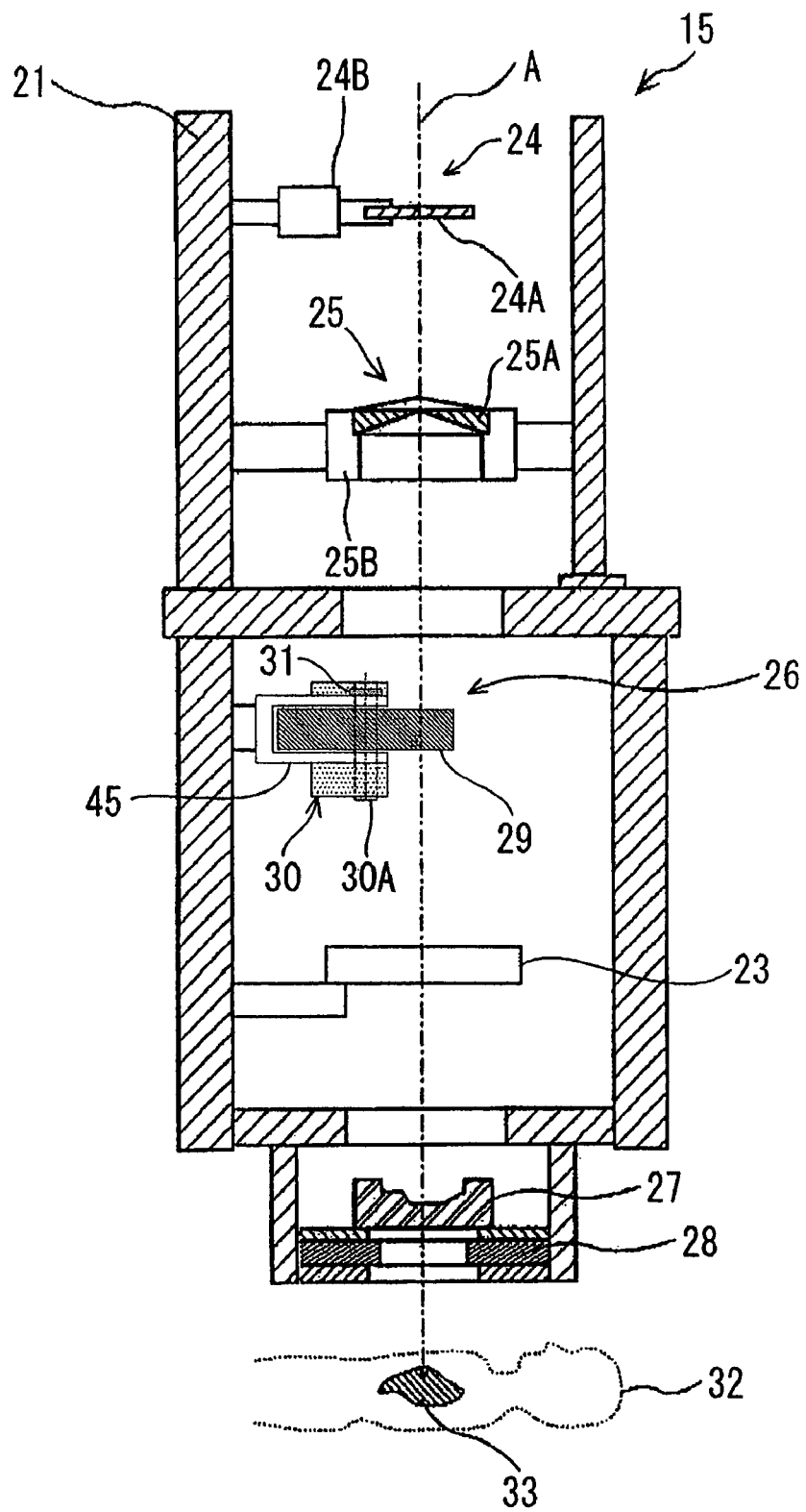
FIG. 2 is a vertical sectional view showing an internal structure of an beam delivery nozzle shown in FIG. 1.

The beam delivery nozzle 15 has a casing 21 (see FIG. 2) mounted to the rotating gantry. Also, the beam delivery nozzle 15 has a first scatterer device 24, a second scatterer device 25, an RMW (range modulation wheel) device 26 serving as a Bragg peak spreading-out device, and a dose monitor 23 as shown in FIG. 2. The first scatterer device 24, the second scatterer device 25, the RMW device 26, and the dose monitor 23 are installed in the casing 21 in this order from the upstream side and are mounted to the casing 21. A bolus 27 and a collimator 28 each formed into a desired shape for each patient are also mounted to the casing 21.

The first scatterer device 24 has a scatterer 24A for spreading out the ion beam in the direction perpendicular to a beam axis A, i.e., a beam path within the casing 21. The scatterer 24A is mounted to the casing 21 through a support member 24B. The scatterer 24A is generally made of a substance (such as lead or tungsten) having the large atomic number, which has a small energy loss with respect to a scattering rate of the ion beam. The first scatterer device 24 is installed such that the scatterer 24A is positioned on the beam axis A.

The second scatterer device 25 has the function of converting the ion beam having a dose distribution, which has been spread into the Gaussian form by the first scatterer device 24, into a uniform dose distribution. The second scatterer device 25 has a scatterer 25A and a support member 25B for mounting the scatterer 25A to the casing 21. The second scatterer device 25 is installed such that the scatterer 25A is positioned on the beam axis A.

Figure 3:
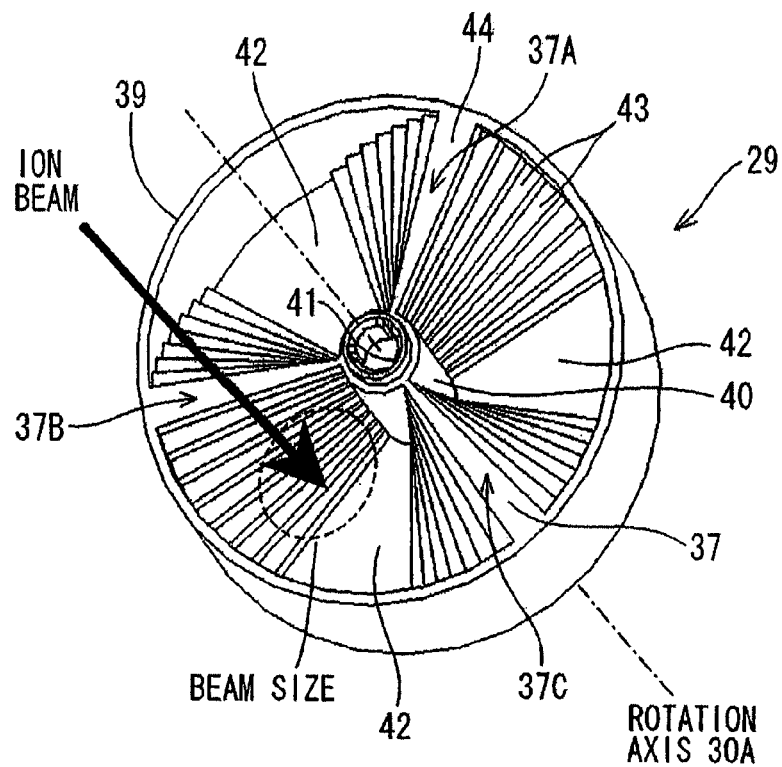
FIG. 3 is a perspective view of an RMW shown in FIGS. 1 and 2.

The RMW device 26 comprises an RMW 29, a rotating device (e.g., a motor) 30 for rotating the RMW 29, and an angle sensor 31 for detecting a rotational phase (angle) of the RMW 29. As shown in FIG. 3, the RMW 29 comprises a plurality of blades (three in this embodiment) 37, a rotating shaft 40, and a cylindrical member 39. The cylindrical member 39 is disposed concentrically with the rotating shaft 40. The plurality of blades 37 (three 37A, 37B and 37C in this embodiment) mounted to the rotating shaft 40 are extended in the radial direction of the RMW 29. An outer end of each of the blades 37 is attached to the cylindrical member 39. Each blade 37 has a circumferential width larger at one end nearer to the cylindrical member 39 than at the other end nearer to the rotating shaft 40. An opening 42 is formed between adjacent two of the blades 37 in the circumferential direction of the RMW 29. Although the RMW of the present embodiment has the opening 42, it is possible that a thin blade with a certain thickness instead of the opening can be applied. In this case, a small amount of energy loss due to the thinnest blade has to be considered. Each blade 37 has a plurality of plane areas (stepped portions) 43 arranged in the form of stairs in the circumferential direction (rotating direction) of the RMW 29. Each of the plane areas 43 has a different thickness relative to a bottom surface of the RMW 29 in the axial direction of the rotating shaft 40 (i.e., the direction of the beam axis A). The thickness of each plane area 43 is called here the plane area thickness. More specifically, the plane area thickness of the blade 37 is increased in a stepwise way from each of the plane areas 43 adjacent to the opening 42, which are positioned on both sides of the blade 37 in the circumferential direction, toward the plane area 43 positioned at a top portion 44 having the largest thickness in the direction of the beam axis A. Each plane area 43 is extended from the rotating shaft 40 toward the cylindrical member 39. In one unit of the RMW 29, three openings 42 are present between the three blades 37.

The rotating shaft 40 is detachably mounted to a support member 45 (FIG. 2) fixed to the casing 21. The rotating shaft 40 has a through hole 41 formed to penetrate the rotating shaft 40 in the axial direction. A rotating shaft 30A of the rotating device 30 mounted to the support member 45 is fitted to the through hole 41. The angle sensor 31 is also mounted on the support member 45.

The RMW 29 may be of a structure having the first scatterer integrally attached to the RMW 29 (e.g., a scatterer affixed to an overall area of the wheel against which the ion beam impinges). Alternatively, a compensator may be attached to the wheel so as to compensate for a difference in scattering rate between the plane areas having large and small values in the thickness distribution.

In the proton beam delivery equipment of this embodiment, a plurality of SOBP (Spread-out Bragg Peak) widths can be produced by making extraction-on/off control of the ion beam from the beam generator 1 in accordance with a rotational angle of the RMW 29. The principle of that operation will be described below with reference to FIGS. 4, 5 and 6.

At the time when the ion beam passes the opening 42 of the RMW 29, the beam energy is not attenuated and therefore the Bragg peak is formed in a deep first position away from the body surface. At the time when the ion beam passes the plane area 43 of the blade 37 which is positioned at the top portion 44 and has the largest thickness, the beam energy is maximally attenuated and therefore the Bragg peak is formed in a shallow second position close to the body surface. At the time when the ion beam passes the plane area 43 positioned between the opening 42 and the top portion 44, the beam energy is attenuated to an extent to the thickness of the blade at the position where the relevant plane area 43 is present, and therefore the Bragg peak is formed in a third position between the first position and the second position. Accordingly, when the ion beam is always in the beam-on state all over a 360°-region of the rotational angle in the circumferential direction of the RMW 29 as the case a shown in FIGS. 4 and 5, the Bragg peak cyclically varies between the first position and the second position with the rotation of the RMW 29. As a result, looking at the dose integrated over time, the case a) can provide a comparatively wide SOBP width ranging from a position near the body surface to a deep position as indicated by a dose distribution a) in the direction of depth, as shown in FIG. 6. The term "beam-on state" means a state in which the ion beam is extracted from the synchrotron 4 and emitted from the beam delivery nozzle 15 after passing the RMW 29. On the other hand, the term "beam-off state" means a state in which the ion beam is neither extracted from the synchrotron 4 nor emitted from the beam delivery nozzle 15.

Figure 4:
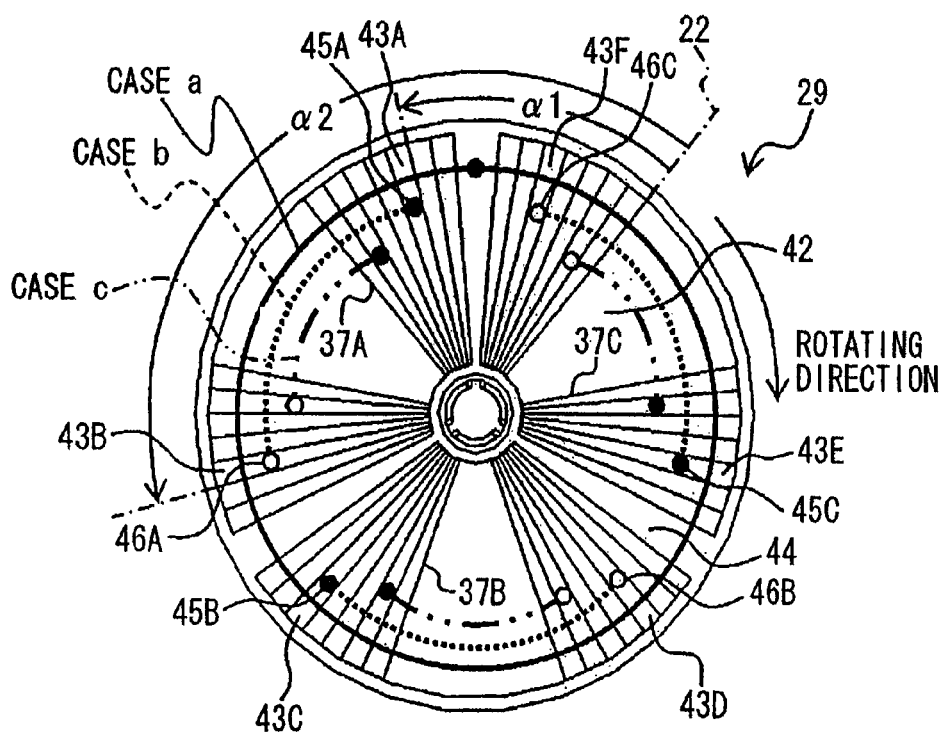
FIG. 4 is a plan view of the RMW shown in FIG. 3, the view showing, by way of example, ion beam emission cases a to c.
Figure 5:
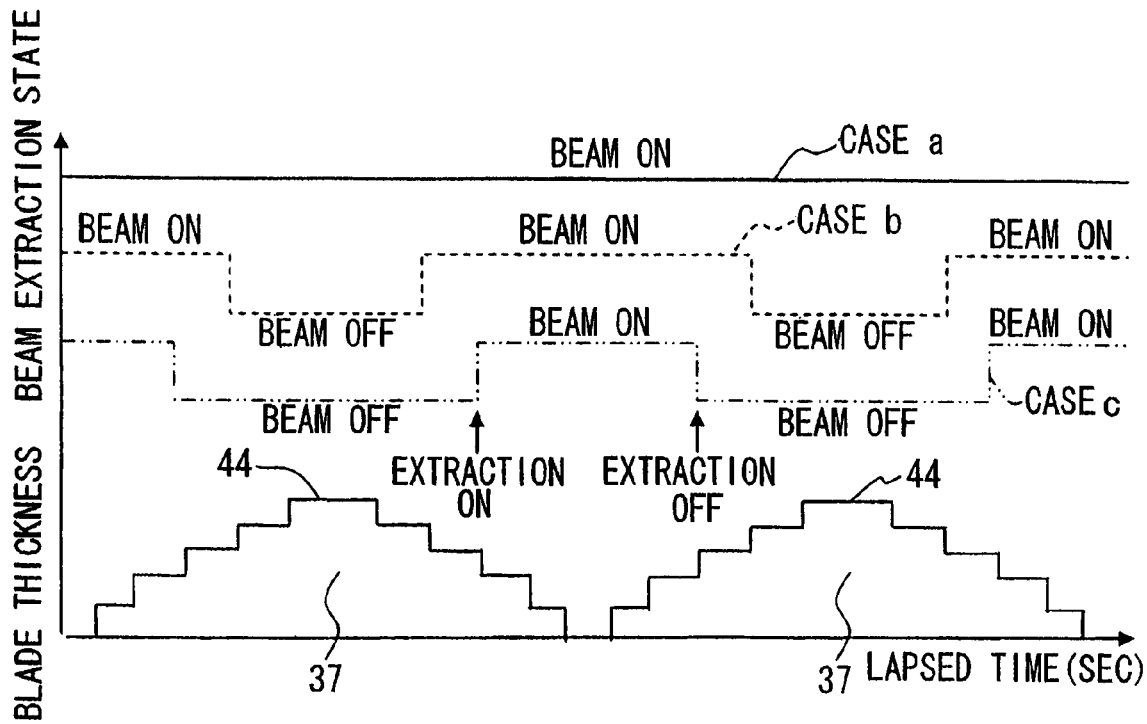
FIG. 5 is a chart showing beam-on and beam-off periods in each of the cases a to c, shown in FIG. 4, on the time serial base.
Figure 6:
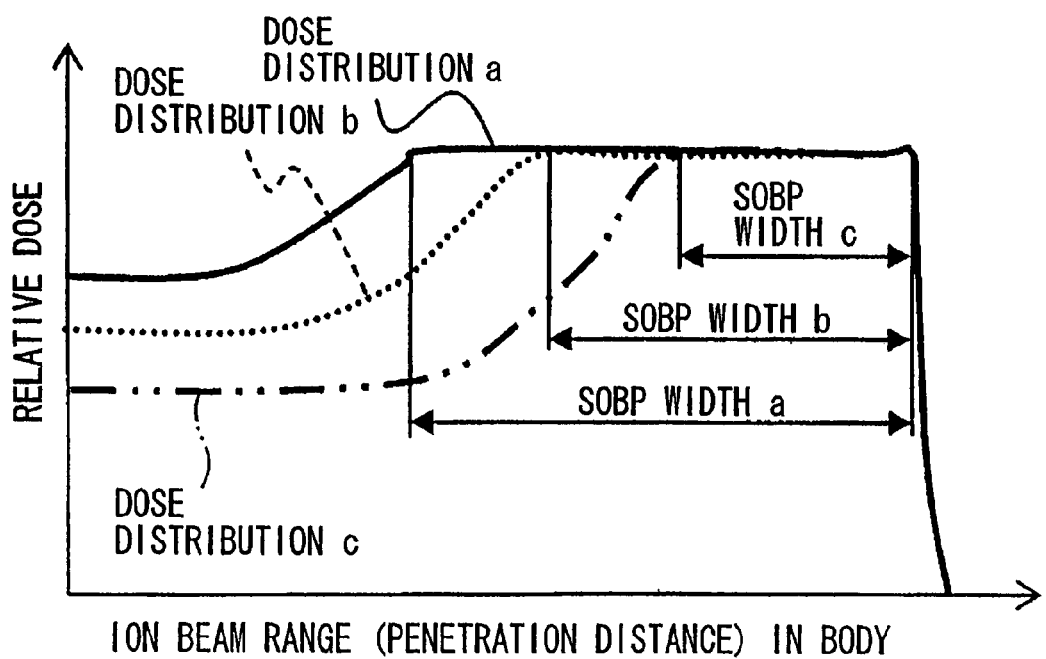
FIG. 6 is a graph showing a dose distribution and a SOBP (spread-out beam peak) width in the direction of depth in each of the cases a to c shown in FIG. 4.

In the case b) shown in FIGS. 4 and 5, the ion beam is brought into the beam-off state in a comparatively thick region (near the top portion 44) of each blade 37 in the circumferential direction of the RMW 29, while the ion beam is brought into the beam-on state in the other region of the rotational angle. Because no Bragg peak is formed in a shallow portion near the body surface, the case b) can provide a SOBP width indicated by a dose distribution b) in the direction of depth and having a narrower flat zone than the dose distribution a) as shown in FIG. 6.

In the case c) shown in FIGS. 4 and 5, the ion beam is brought into the beam-on state in the opening 42 and a comparatively thin region of each blade 37 near the opening 42 in the circumferential direction of the RMW 29, while the ion beam is brought into the beam-off state in the other region of the rotational angle. Because the attenuation of the beam energy is small as a whole, the Bragg peak is formed in a deep position away from the body surface. Therefore, the case c) can provide a SOBP width indicated by a dose distribution c) in the direction of depth and having a narrower flat zone than the dose distribution b) as shown in FIG. 6.

Thus, the proton beam delivery equipment 7 can form a plurality of different SOBP widths with one RMW 29 by making extraction-on/off control of the ion beam in accordance with the rotational angle of the RMW 29 as described above.

Returning to FIG. 2, the dose monitor 23 measures dose of the ion beam in the irradiation field formed by the SOBP device 26, etc. The bolus 27 has the function of making the penetration depth distribution of the ion beam match distal depth variation of a diseased part (i.e., a tumor or a cancer) 33 in the body of the patient 32 under treatment. Stated another way, the bolus 27 adjusts the penetrating range distribution of the ion beam to the shape of the tumor 33 as an irradiation target in the direction of depth. The bolus 27 is also called a range compensating device, an energy compensator, or a compensator. The collimator 28 shapes the ion beam at each position in match with the shape of the tumor 33 in the direction perpendicular to the beam path (beam axis A).

Prior to starting irradiation of the ion beam from the beam delivery nozzle 15, the treatment couch 34 on which the patient is lying is moved by a couch driving device (not shown) into the treatment cage. The rotating gantry is rotated by a motor (not shown) to direct the beam path within the beam delivery nozzle 15 toward the tumor 33 in the body of the patient 32 lying on the treatment couch 34. Further, the treatment couch 34 is positioned relative to the beam delivery nozzle 15 so that the tumor in the body of the patient is aligned with the beam path within the beam delivery nozzle 15 at high accuracy. Then, the ion beam introduced to the beam delivery nozzle 15 through the beam passage 16 is delivered to the tumor 33 after passing the first scatterer device 24, the second scatterer device 25, the RMW device 26 in which the RMW 29 is rotating, the bolus 27, and the collimator 28, which are all installed in the beam delivery nozzle 15. The RMW 29 is rotated by the rotating device 30.

The extraction-on/off control of the ion beam during the rotation of the RMW 29 in this embodiment will be described in more detail below. The term "extraction-on of the ion beam" means the start of extraction of the ion beam from the synchrotron 4, and the term "extraction-off of the ion beam" means the stop of extraction of the ion beam from the synchrotron 4. First, a tomogram of the tumor 33 in the body of the patient 32 and thereabout is taken by using an X-ray CT apparatus (not shown). A physician makes a diagnosis based on the obtained tomogram to confirm the position and size of the tumor 33, and determines the direction of irradiation of the ion beam, the maximum irradiation depth, etc., followed by inputting them to a treatment planning unit 35. Based on the input data such as the direction of irradiation of the ion beam and the maximum irradiation depth, the treatment planning unit 35 computes factors necessary for the treatment, such as the SOBP width, the irradiation field size, and the target dose to be irradiated to the tumor 33, by using treatment planning software. Further, by using the treatment planning software, the treatment planning unit 35 computes various operation parameters (such as the beam energy when the ion beam is extracted from the synchrotron 4 (i.e., the extraction energy), the angle of the rotating gantry, patient couch position and the rotational angles of the RMW 29 when the extraction of the ion beam is turned on and off), and then selects the RMW 29 having a thickness distribution and an angular width in the circumferential direction suitable for the treatment. Various items of treatment plan information computed by the treatment planning unit 35, such as the extraction energy, the SOBP width, the irradiation field size, the rotational angles, the patient couch position and the irradiation dose, are inputted to a central processing unit 36 of the proton beam delivery equipment 7 and stored in a memory (not shown) of the central processing unit 36.

Those various items of treatment plan information are displayed on a display of the treatment planning unit 35 and on a display installed in a control room of the proton beam delivery equipment 7. Then, the RMW 29, the bolus 27, and the collimator 28 suitable for the patient 32, who is going to take treatment, are installed in the casing 21 of the beam delivery nozzle 15 by an operator, as shown in FIG. 2.

An irradiation controller 38 receives, from the central processing unit 36, setting values of required treatment plan information, i.e., rotational angles (e.g., $\alpha 1$ to $\alpha 6$ described later) of the RMW 29, a target dose, an angle of the rotating gantry, and a patient couch position and then stores the input data in the memory (not shown) of the irradiation controller 38. A gantry controller (not shown) receives the rotating gantry angle information from the irradiation controller 38 and rotates the rotating gantry based on the rotating gantry angle information, as described above, so that the beam path within the beam delivery nozzle 15 is directed toward the tumor 33. Based on information of the extraction energy irradiated to the patient 32, the central processing unit 36 sets control commands for currents (i.e., current setting values) introduced to the respective magnets of the beam generator 1 and the beam transport system 2. In accordance with the current setting values, a magnet power supply controller (not shown) controls respective power supplies for the corresponding magnets and adjusts values of excitation currents supplied to the respective magnets of the beam generator 1 and the beam transport system 2. Preparations for introducing the ion beam to the beam generator 1 and the beam transport system 2 are thereby completed. The magnet power supply controller is connected to the central processing unit 36.

The synchrotron 4 is operated by repeating the steps of injecting the ion beam from the pre-accelerator 3, and then accelerating, extracting and decelerating (preparation of next injecting) the ion beam. When the ion beam is accelerated until reaching the desired extraction energy at a setting level, the acceleration of the ion beam is brought to an end and the ion beam comes into a state ready for extraction from the synchrotron 4 (i.e., an ion beam extractable state). Information indicating the end of acceleration of the ion beam is transmitted to the central processing unit 36 from the magnet power supply controller that monitors states of the magnets, etc. of the synchrotron 4 using status sensors (not shown).

The extraction-on/off control of the ion beam for forming the SOBP width in the proton beam delivery equipment 7 will be described below with reference to FIGS. 1, 2, 4 and 7. The following description of the extraction-on/off control of the ion beam is made, by way of example, in connection with the case b shown in FIG. 4. In the example of the case b), points 45A, 45B and 45C each represent the timing of the extraction-on (start of extraction) of the ion beam, while points 46A, 46B and 46C each represent the timing of the extraction-off (stop of extraction) of the ion beam. When the irradiation controller 38 executes the control for the case b, it receives beforehand the rotational angles $\alpha 1$ to $\alpha 6$ ($\alpha 3$ to $\alpha 6$ are not shown), i.e., the setting values of the rotational angles, from the central processing unit 36. The rotational angle $\alpha 1$ represents an angle from a reference line 22 to the point 45A, and the rotational angle $\alpha 2$ represents an angle from the reference line 22 to the point 46A. The rotational angle $\alpha 3$ represents an angle from the reference line 22 to the point 45B, and the rotational angle $\alpha 4$ represents an angle from the reference line 22 to the point 46B. The rotational angle $\alpha 5$ represents an angle from the reference line 22 to the point 45C, and the rotational angle $\alpha 6$ represents an angle from the reference line 22 to the point 46C. The rotational angles $\alpha 1$ to $\alpha 6$ each represent an angle on the basis of the state in which the reference line 22 is positioned on the beam axis A.

Figure 7:
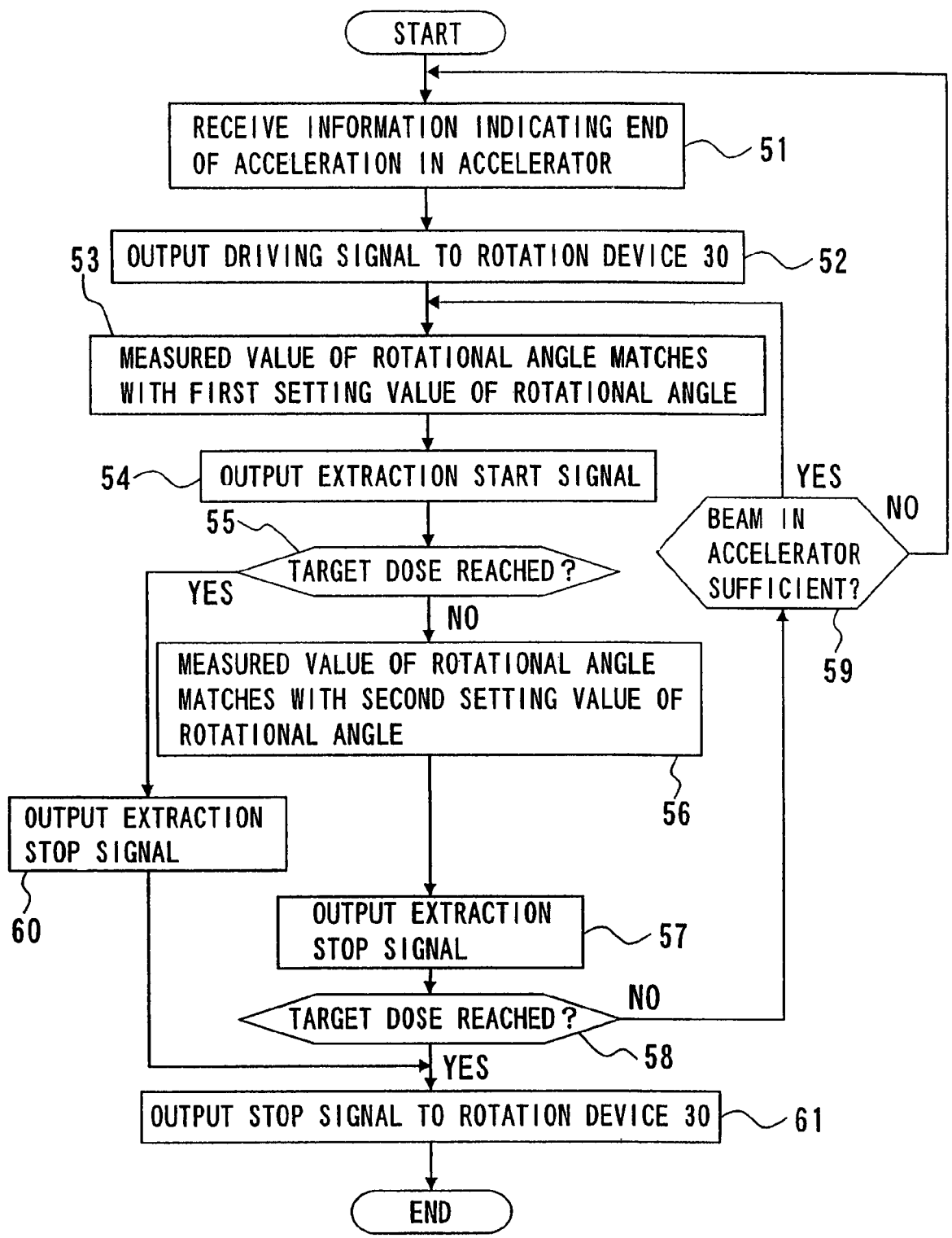
FIG. 7 is a flowchart showing control steps executed by an irradiation controller shown in FIG. 1.

The irradiation controller 38 executes the extraction-on/off control of the ion beam in accordance with a control flow shown in FIG. 7. First, the irradiation controller 38 receives a signal indicating the end of acceleration in the accelerator (synchrotron 4) (i.e., a signal indicating that the ion beam is in the extractable state) (step 51). The end-of-acceleration signal is inputted from the central processing unit 36. The irradiation controller 38 outputs a start-of-rotation signal to the rotating device 30 (step 52). The rotating device 30 is rotated in accordance with a drive signal outputted from the irradiation controller 38. The torque of the rotating device 30 is transmitted to the rotating shaft 40 of the RMW 29 through the rotating shaft 30A, whereby the RMW 29 is rotated. The number of rotations of the RMW 29 is set to the range of 10 to 20 rotations per second. It is determined whether a measured value of the rotational angle matches with a first setting value of the rotational angle (step 53). More specifically, the measured value of the rotational angle of the RMW 29 measured by the angle sensor 31 is inputted to the irradiation controller 38. It is then determined whether the input measured value matches with the first setting value of the rotational angle (any of the rotational angles $\alpha 1$, $\alpha 3$ and $\alpha 5$) at which a beam extraction start signal is to be outputted. If the measured value of the rotational angle matches with the first setting value, the beam extraction start signal is outputted (step 54). The on/off switch 9 is closed in response to the beam extraction start signal. An RF power from the RF-applying device 5 is applied to the circulating ion beam, whereupon the ion beam is extracted from the synchrotron 4. The extracted ion beam is transported to the beam delivery nozzle 15. After passing the rotating RMW 29, etc. within the beam delivery nozzle 15, the ion beam is emitted from the beam delivery nozzle 15 along the beam axis A and then delivered to the tumor 33. In FIG. 4, a black circle represents the position where the extraction of the ion beam is started.

It is determined whether a dose delivered to the tumor 33 has reached the target dose (step 55). Further, it is determined whether the measured value of the rotational angle matches with a second setting value of the rotational angle (step 56). The dose irradiated to the tumor 33, which is measured by the dose monitor 23, and the measured value of the rotational angle are always inputted to the irradiation controller 38. In step 55, it is determined whether an accumulated value of the measured dose has reached the target dose. If this determination result is "YES", the processing of step 60 is executed in precedence to the processing of step 56 and a beam extraction stop signal is outputted. In response to the beam extraction stop signal, the on/off switch 9 is opened to stop the supply of the RF power to the RF-applying device 5. Accordingly, the extraction of the ion beam from the synchrotron 4 is stopped and the irradiation of the ion beam toward the patient 32 lying on the treatment couch 34 is brought to an end. A stop-of-rotation signal is then outputted to the rotating device 30 (step 61). Thereby, the rotation of the rotating device 30 is stopped and the rotation of the RMW 29 is also stopped.

If the determination result in step 55 is "NO", the processing of step 56 is executed. If it is determined in step 56 that the measured value of the rotational angle matches with the second setting value of the rotational angle (any of the rotational angles $\alpha 2$, $\alpha 4$ and $\alpha 6$) at which the beam extraction stop signal is to be outputted, the beam extraction stop signal is outputted (step 57). In response to the beam extraction stop signal, as mentioned above, the on/off switch 9 is opened and the extraction of the ion beam from the synchrotron 4 is stopped. In FIG. 4, a white circle represents the position where the extraction of the ion beam is stopped. The period from the output of the beam extraction start signal in step 54 to the output of the beam extraction stop signal in step 57 represents a period during which, for example, a region from the plane area 43A of the blade 37A to the plane area 43B of the blade 37B intersects the beam axis A along which the ion beam travels, i.e., an effective beam-on period. The time taken from the closing of the on/off switch 9 to the start of extraction of the ion beam from the synchrotron 4 is not longer than $1/1000$ sec, and conversely the time taken from the opening of the on/off switch 9 to the stop of extraction of the ion beam is also not longer than $1/1000$ sec.

In step 58, it is determined again whether the dose irradiated to the tumor 33 has reached the target dose. If this determination result is "NO", the processing of step 59 is executed. Stated another way, it is determined whether a sufficient amount of the ion beam exists in the synchrotron 4 after the end of the beam-on period. The amount of the ion beam (i.e., the current density of the ion beam) is monitored by the magnet power supply controller based on a value measured by a sensor (not shown) disposed in the synchrotron 4. The measured value of the current density of the ion beam is inputted to the irradiation controller 38 via the central processing unit 36. The determination in step 59 is made using the measured value of the current density. If the determination result in step 59 is "YES", the processing of steps 53 to 58 is executed again. The period from the output of the beam extraction start signal in step 54 to the output of the beam extraction stop signal in step 57 in this repeated process represents a period during which, for example, a region from the plane area 43C of the blade 37B to the plane area 43D of the blade 37C intersects the beam axis A, i.e., an effective beam-on period. The period during which, for example, a region from the plane area 43E of the blade 37C to the plane area 43F of the blade 37A intersects the beam axis A in the next repeated process of steps 53 to 58 also represents an effective beam-on period. Between the two beam-on periods adjacent to each other, there is a beam-off period as shown in FIG. 5. If, during the repeated process of steps 53 to 58, it is determined in step 55 or 58 that an accumulated value of the measured dose has reached the target dose, the processing of step 61 is executed and the irradiation of the ion beam toward the patient 32 is brought to and end.

If the determination result in step 59 is "NO", the processing subsequent to step 51 is executed. More specifically, if the current density of the ion beam circulating within the synchrotron 4 lowers and the extraction of the ion beam is disabled, the ion beam in the synchrotron 4 is decelerated. The magnet power supply controller reduces the current values supplied to the magnets disposed in the synchrotron 4, the beam transport system 2, etc. The current values supplied to those magnets are held in the state allowing the ion beam to enter. The ion beam is introduced to the synchrotron 4 from the pre-accelerator 3. Then, the ion beam is accelerated until reaching the extraction energy, as described above. After the end of acceleration of the ion beam, the processing subsequent to step 51 is executed by the irradiation controller 38.

Because the determination in step 55 is made between steps 54 and 56, the extraction of the ion beam can be stopped when the accumulated value of the measured dose has reached the target dose during the period in which the ion beam passes the rotating RMW 29. It is hence possible to prevent the ion beam from being excessively delivered to the tumor 33. For example, if the determination result in step 55 is made "YES" when the opening 42 between the blade 37A and the blade 37B, shown in FIG. 4, is positioned on the beam axis A, the extraction of the ion beam can be stopped immediately. Therefore, the irradiation of the ion beam to the tumor 33 can be avoided during the period from the time at which the opening 42 is positioned on the beam axis A to the time at which the point 46A corresponding to the second setting value of the rotational angle is positioned on the beam axis A.

In the example of the case b) described above, the region from the point 45A to the point 46A, the region from the point 45B to the point 46B, and the region from the point 45C to the point 46C each represent an ion beam passage region in the RMW 29. The region from the point 46A to the point 45B, the region from the point 46B to the point 45C, and the region from the point 46C to the point 45A each represent a region in the RMW 29 where the ion beam does not pass (i.e., an ion beam non-passage region). While the above description is made, by way of example, in connection with the case b, various SOBP widths can be formed by changing, for one unit of the RWM 29, the first setting values of the rotational angle at each of which the beam extraction start signal is to be outputted and the second setting values of the rotational angle at each of which the beam extraction stop signal is to be outputted. While the ion beam passes the opening 42 in each of the "beam-on" periods shown in FIG. 5, the irradiation controller 38 may execute control such that the ion beam passes the top portion 44 of the blade in each of the "beam-on" periods instead of passing the opening 42. In such a case, for example, the irradiation controller 38 outputs the beam extraction start signal when the point 46C shown in FIG. 4 has reached the position of the beam axis A, and outputs the beam extraction stop signal when the point 45A shown in FIG. 4 has reached the position of the beam axis A.

With the proton beam delivery equipment 7 of this embodiment, since the on/off control of the ion beam is performed with the RMW 29 being rotated, the region in the RMW 29 where the ion beam passes the RMW 29 can be varied in the rotating direction of the RMW 29. Accordingly, a plurality of SOBP widths having different values in the direction of depth from the body surface of the patient 32 can be formed by using one RMW 29, and one RMW 29 can be used for a plurality of patients. In other words, the number of patients treatable using one RMW 29 is increased. Also, since a plurality of SOBP widths can be formed by using one RMW 29, it is possible to reduce the number of RMWs to be prepared in a cancer treatment center equipped with the proton beam delivery equipment 7. Further, since a plurality of SOBP widths can be formed by using one RMW 29, it is possible to reduce the number of times at which the RMW installed in the beam delivery nozzle 15 is to be replaced. This is advantageous in cutting the time required for preparations of the treatment and in increasing the number of patients treated by the proton beam delivery equipment 7. Especially, in this embodiment, since the on/off control of the ion beam is performed in accordance with the rotational angle (specifically the measured values and the setting values of the rotational angle) of the RMW 29, each particular SOBP width can be formed at high accuracy. By changing the rotational angle of the RMW in the on/off control of the ion beam, the SOBP widths having various values can be formed.

In the synchrotron 4, the number of accelerated ions is constant. Therefore, even when the beam-on period is shortened, the current density of the ion beam extracted from the synchrotron 4 during the beam-on period can be increased by increasing the RF power supplied from the first RF-power supply 8 to the RF-applying device 5. Hence, the dose rate for irradiation to the patient (i.e., the radiation dose irradiated to the patient per unit time and per unit volume) can be increased even in a short beam-on period. In other words, the irradiation time of the ion beam can be reduced for the patient 32 having the tumor 33 with a small thickness or a small volume by irradiating the ion beam having the increased current density. This reduction of the irradiation time contributes to reducing the burden imposed on the patient 32 and increasing the number of patients treated per year. Further, even in the case of shortening the beam-on period, all of the circulating ion beam can be essentially extracted from the synchrotron 4 by increasing the RF power for the beam extraction as mentioned above. As a result, the degree of radiation accumulated in the components, such as the synchrotron 4, can be reduced.

As an accelerator, a cyclotron may also be used, instead of the synchrotron, for introducing an ion beam extracted from the cyclotron to the beam delivery nozzle 15. However, the cyclotron does not include the decelerating step unlike the synchrotron, and performs steps of entering, accelerating and extracting the ion beam in succession. Accordingly, if the "beam-on" period is shortened, the number of ions extracted from the beam delivery nozzle 15 per unit time is reduced, while the rate of dose irradiated to the tumor 33 is not changed. This results in a reduction of the SOBP width and is hence equivalent to a reduction of the volume subjected to the irradiation. As a result, even when the "beam-on" period is shortened, the irradiation time of the ion beam is not changed for the patient 32 having the tumor 33 with a small thickness or a small volume. If the extraction of the ion beam is turned off during or after the step of accelerating the ion beam in the cyclotron, the amount of the ion beam discarded is increased and the degree of radiation accumulated in the components, such as various units of the cyclotron, is increased.

Figure 8:
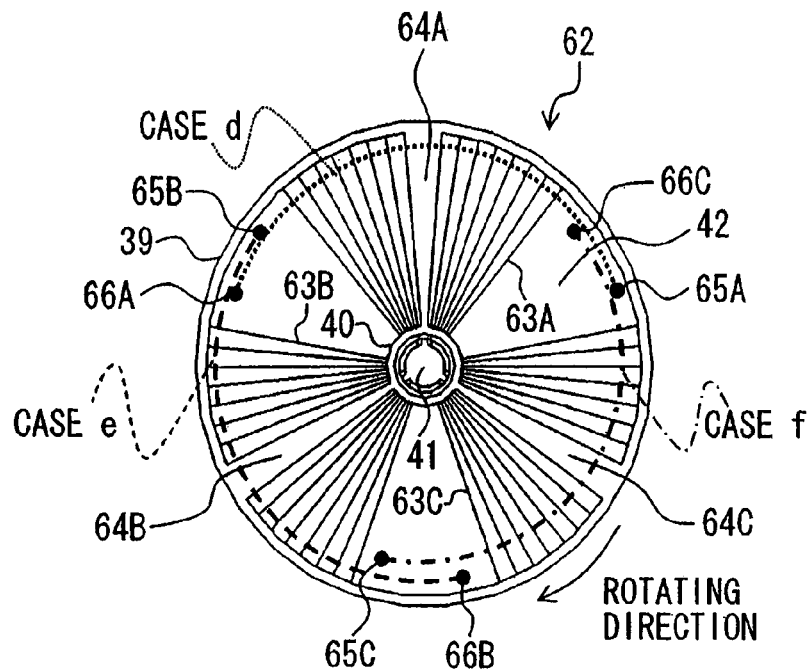
FIG. 8 is a plan view of another example of the RMW, the view showing, by way of example, ion beam emission cases d to f.
Figure 9:
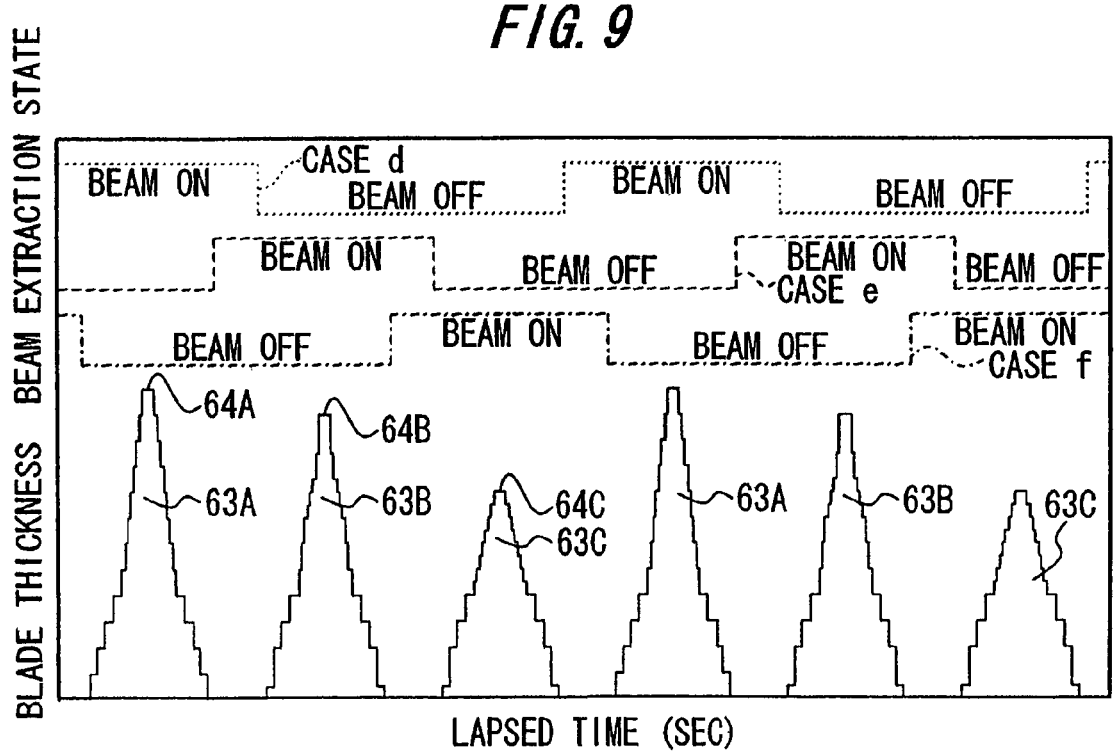
FIG. 9 is a chart showing beam-on and beam-off periods in each of the cases d to f, shown in FIG. 8, on the time serial base.

A description is now made of a modification of the first embodiment in which another RMW 62 shown in FIG. 8 is used instead of the RMW 29. The RMW 62 has three blades 63A, 63B and 63C. Numerals 64A, 64B and 64C denote respective top portions of the blades 63A, 63B and 63C. The blades 63A, 63B and 63C have different values of thickness from their bottom surfaces to their top portions. As shown in FIG. 9, the thickness of the blade 63A is maximum, the thickness of the blade 63B is medium, and the thickness of the blade 63C is minimum. Similarly to the RMW 29, each of the blades 63A, 63B and 63C has a plurality of plane areas. The other construction of the RMW 62 is the same as that of the RMW 29. While all the top portions of the blades of the RMW 29 have the same height, the top portions of the blades of the RMW 62 have heights different from one another. The RMW 62 is also detachably mounted to the support member 45 within the beam delivery nozzle 15.

When the RMW 62 is installed in the beam delivery nozzle 15, the extraction-on/off control of the ion beam is performed in three cases described below. In case d), the beam extraction start signal is outputted at the rotational angle indicated by the position of a point 65A, and the beam extraction stop signal is outputted at the rotational angle indicated by the position of a point 66A, thereby providing the "beam-on" state in a region including the blade 63A. In case e), the beam extraction start signal is outputted at the rotational angle indicated by the position of a point 65B, and the beam extraction stop signal is outputted at the rotational angle indicated by the position of a point 66B, thereby providing the "beam-on" state in a region including the blade 63B. In case f), the beam extraction start signal is outputted at the rotational angle indicated by the position of a point 65C, and the beam extraction stop signal is outputted at the rotational angle indicated by the position of a point 66C, thereby providing the "beam-on" state in a region including the blade 63C. The points 65A to 65C and 66A to 66C are each positioned in a corresponding one of the openings 42. In any case, the ion beam is in the "beam-off" state in the other region than the "beam-on" state.

The extraction-on/off control of the ion beam in the case d) to f) is executed by the irradiation controller 38 through the processing in accordance with the flowchart shown in FIG. 7. The modification using the RMW 62 can also provide similar advantages to those described above in connection with the first embodiment. In short, the RMW 62 enables three different SOBP widths corresponding to the blades 63A, 63B and 63C to be formed by using one RMW.

While the RMW 62 has the three blades having different heights from one another, it may have two, four or more blades having different heights from one another. Also, while the "beam-on" region in the RMW 62 is set only in the region including only one blade, the "beam-on" region may be set over two or more adjacent blades having different heights from one another. In such a case, when the "beam-on" region is set over, e.g., the blades 63A and 63B, a resulting dose distribution is one obtained by superimposing respective dose distributions with each other, which are obtained by separately irradiating the ion beam to those blades. Additionally, the "beam-on" region is not always required to include the whole of any of the blades, and the "beam-on" region may be set to cover parts of the adjacent blades as in the RMW 29.

Second Embodiment

Figure 10:
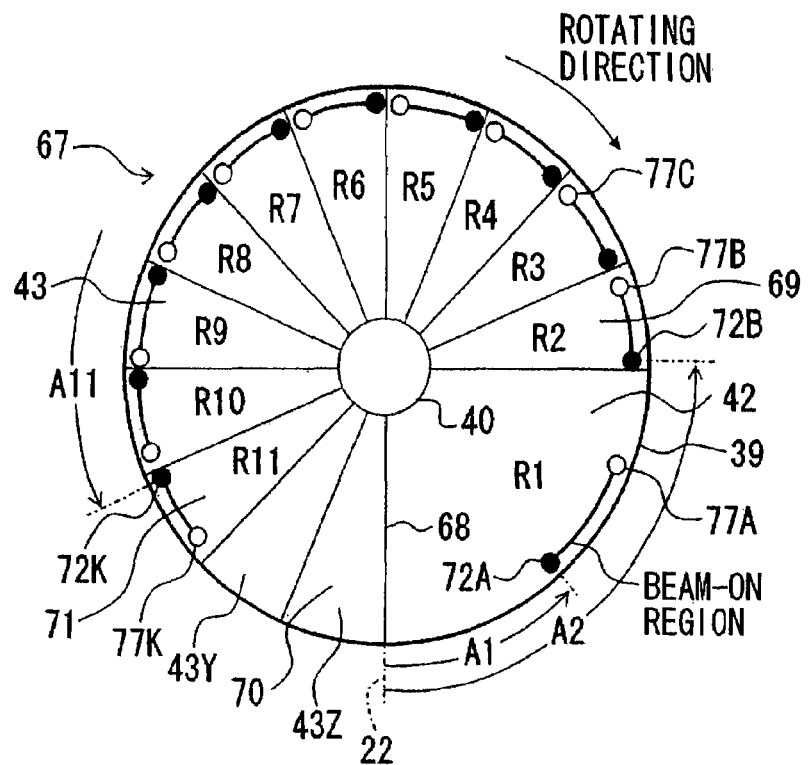
FIG. 10 is a plan view of an RMW used in ion beam delivery equipment according to a second embodiment of the present invention, the view showing, by way of example, one ion beam emission case.
Figure 11:
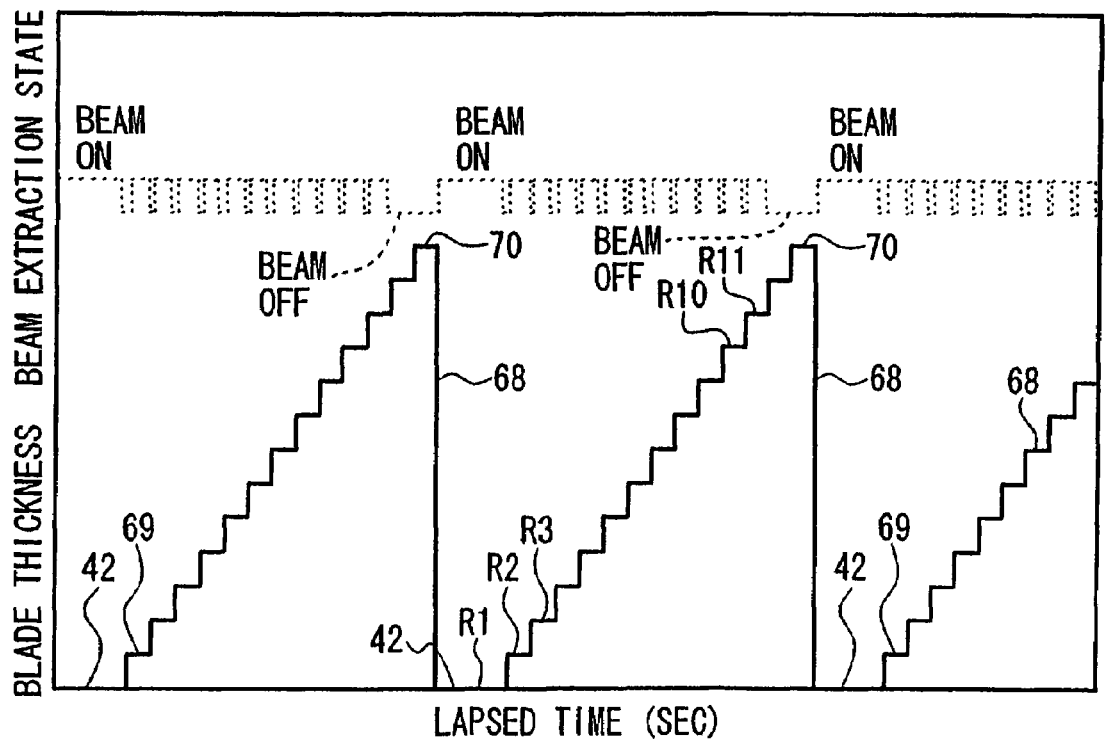
FIG. 11 is a chart showing beam-on states in the case shown in FIG. 10.

Proton beam delivery equipment according to a second embodiment, i.e., another embodiment of the present invention, will be described below. In the proton beam delivery equipment of this second embodiment, an RMW 67 shown in FIG. 10 is substituted for the RMW 29 installed in the beam delivery nozzle 15 in the proton beam delivery equipment 7 of the first embodiment. The other construction of the proton beam delivery equipment of this second embodiment is the same as that of the proton beam delivery equipment 7. In the proton beam delivery equipment of this second embodiment, as shown in FIG. 11, the beam extraction-on/off control is performed for each stepped portion (plane area) of the RMW 67.

The RMW 67 includes one blade 68 having a plurality of plane areas 43 formed such that a thickness of each plane area in the axial direction is increased step by step from the opening 42 having a thickness being 0 to a top portion 70 having a maximum thickness in a direction opposed to the rotating direction of the RMW 67. The other construction of the RMW 67 is the same as that of the RMW 29 and hence is not described here.

Figure 12:
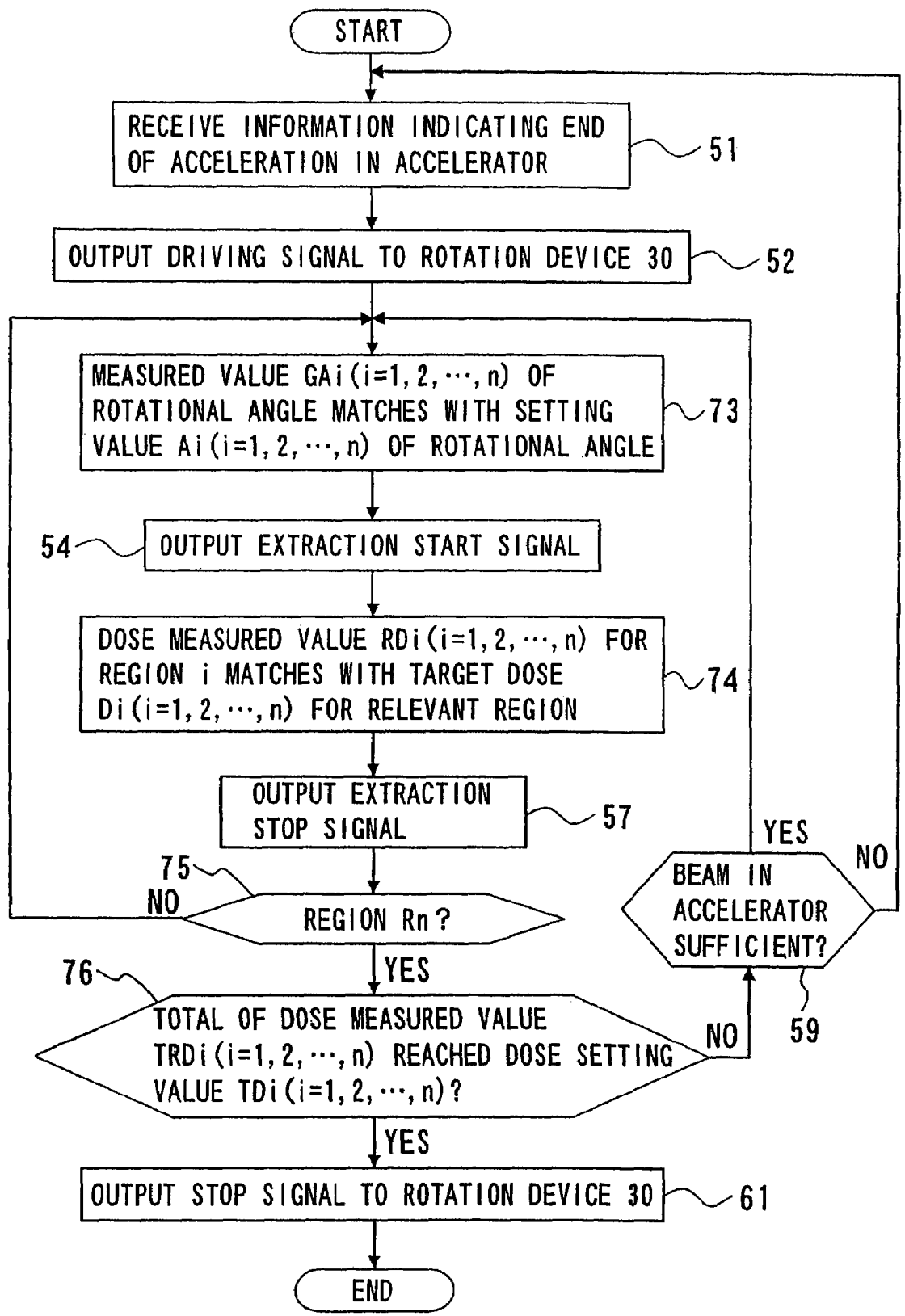
FIG. 12 is a flowchart showing control steps executed by an irradiation controller shown in the second embodiment.

The extraction-on/off control of the ion beam executed by the irradiation controller 38 in this embodiment will be described below with reference to a control flow shown in FIG. 12. Of the control flow shown in FIG. 12, the same part as that of the control flow shown in FIG. 7 is not described here.

The irradiation controller 38 receives beforehand, as treatment plan information, information indicating a beam-on region Ri (i=1, 2, . . . , n) (where n is an integer) from the central processing unit 36. The treatment plan information further includes a setting value Ai (i=1, 2, . . . , n) of the rotational angle and a target dose value Di (i=1, 2, . . . , n), both described later, which are also inputted beforehand to the irradiation controller 38 from the central processing unit 36. In a treatment example described here, the beam-on region Ri is set to, e.g., R11, namely 11 regions ranging from the region R1 to the region R11 as shown in FIG. 10. The setting n=11 is also applied to the setting value Ai of the rotational angle and the target dose value Di. The region R1 is positioned in the opening 42. The region R2 to the region R11 circumferentially cover the blade 68 from the plane area 43 located at a position 69 where the blade thickness is minimum, to the plane area 43 located at a position 71 where the blade thickness is third largest. Also, the rotational angles A1 to A11, i.e., the setting values of the rotational angle, each represent an angle from a reference line 22 to the position of a corresponding black circle; namely, the rotational angle A1 represents an angle from the reference line 22 to a point 72A, the rotational angle A2 represents an angle from the reference line 22 to a point 72B, and the rotational angle A11 represents an angle from the reference line 22 to a point 72K. Alternatively, depending on the size of the tumor 33 in the body of the patient 32 and the position of the tumor from the body surface, the beam-on region Ri (i=1, 2, . . . , n) may be set to cover, for example, from the region R4 to the top portion 70, or from the region R3 to the region R9 in FIG. 10.

The irradiation controller 38 receives a signal indicating the end of acceleration in the accelerator (synchrotron 4) (step 51). Then, the irradiation controller 38 outputs a start-of-rotation signal to the rotating device 30 (step 52). The rotating device 30 rotates the RMW 67 at the number of, e.g., six rotations per second. It is determined whether a measured value GAi (i=1, 2, . . . , n) of the rotational angle matches with a setting value Ai (i=1, 2, . . . , n) of the rotational angle (step 73). If the measured value GAi of the rotational angle of the RMW 67 measured by the angle sensor 31, for example, matches with the setting value Ai of the rotational angle, a beam extraction start signal is outputted (step 54). As one example, at the time when the measured value GA1 matches with the setting value A1, the beam extraction start signal is outputted. The on/off switch 9 is closed in response to the beam extraction start signal, whereupon the ion beam is extracted from the synchrotron 4. The extracted ion beam is irradiated to the tumor 33 after passing the region Ri (e.g., the region R1 corresponding to the opening 42) of the RMW 67.

It is determined whether a measured dose value RDi (i=1, 2, . . . , n) for the region Ri matches with the target dose Di (i=1, 2, . . . , n) for the same region Ri (step 74). The measured dose value RDi of the ion beam irradiated to the tumor 33, which is obtained from the dose monitor 23, is inputted to the irradiation controller 38. If the measured dose value RDi matches with the target dose Di, a beam extraction stop signal is outputted (step 57). For example, at the time when the measured dose value RD1 for the region R1 matches with the target dose D1 for the same region R1, the beam extraction stop signal is outputted. In response to the beam extraction stop signal, the on/off switch 9 is opened to stop the extraction of the ion beam from the synchrotron 4. With the above-described processing of steps 73, 54, 74 and 57, the ion beam passes the region R1 in the range of the rotational angle from the black-circle point 72A to a white-circle point 77A for irradiation to the tumor 33. The ion beam having passed the region R1 (i.e., the opening 42) is irradiated to the deepest position of the tumor 33 because beam energy is not attenuated by the RMW 67. If the determination result in step 75 is "NO" (i.e., if the region Rn is not yet reached), the processing of steps 73, 54, 74, 57 and 75 is repeatedly executed for the regions R2, R3, . . . , Rn in succession. In this example, the processing is repeated until reaching the region R11. With the processing of steps 73, 54, 74 and 57 repeated, the ion beam passes successively the region R2 in the range of the rotational angle from a black-circle point 72B to a white-circle point 77B, the region R3 in the range of the rotational angle from a black-circle point 72C to a white-circle point 77C, . . . , and finally the region R11 in the range of the rotational angle from a black-circle point 72K to a white-circle point 77K. In this example, because the extraction of the ion beam is turned off in a plane area 43Z corresponding to the flat portion 70 of the RMW 67 and a plane area 43Y at a level one step lower than the flat portion 70, the ion beam does not pass those plane areas 43Z, 43Y.

If the determination result in step 75 is "YES" (i.e., if the region Rn has been reached), the processing of step 76 is executed to determine whether an accumulated value TRDi (i=1, 2, . . . , n) of the measured dose for the region Ri has reached a dose setting value TDi (i=1, 2, . . . , n) for the same region Ri. If the determination result in step 76 is "NO", the determination in step 59 is made. If the determination result in step 59 is "YES", the processing of steps 73, 54, 74, 57, 75 and 76 is repeated. If the determination result in step 59 is "NO", the processing of steps 51 to 76 shown in FIG. 12 is repeated. If the determination result in step 76 is "YES", a stop-of-rotation signal is outputted to the rotating device 30 (step 61) and the irradiation of the ion beam to the patient 32 is brought to an end.

Figure 13:
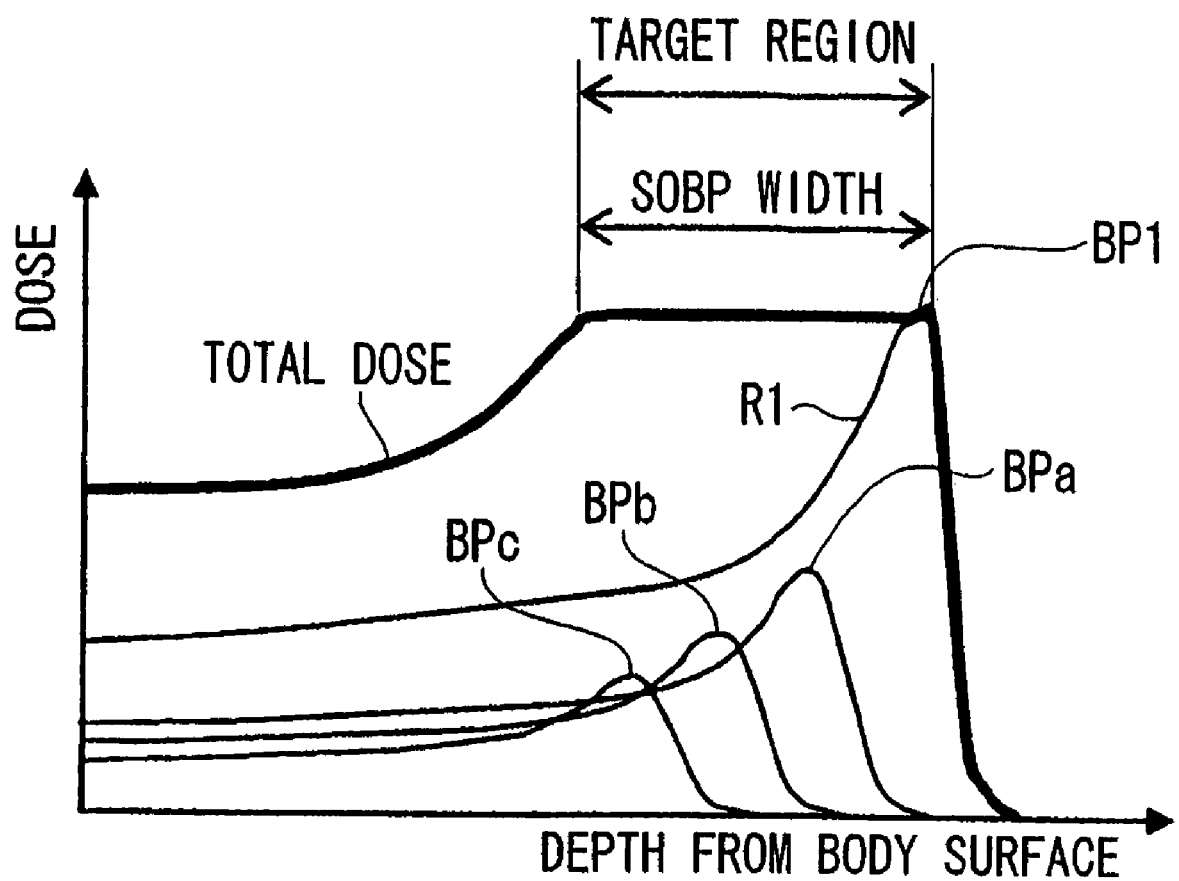
FIG. 13 is an explanatory graph showing dose of each Bragg peak.

With reference to FIG. 13, a description is now made of the target dose Di (i=1, 2, . . . , n) and the dose setting value TDi (i=1, 2, . . . , n) for each region Ri (i=1, 2, . . . , n). The SOBP width, i.e., the zone where the total dose has a uniform distribution in the direction of depth from the body surface of the patient 32, is set so as to include the width of the tumor (target area) 33 in the direction of depth. The total dose means a total of dose irradiated in the form of the ion beam to the tumor 33. As shown in FIG. 13, the ion beam having passed the region R1 (i.e., the opening 42) of the RMW 67 forms a Bragg peak at the deepest position of the tumor 33. The dose of a Bragg peak BP1 shown in FIG. 13 represents a total dose irradiated to the tumor 33 as the ion beam having passed the region R1 until the irradiation of the ion beam to the tumor 33 is completed. The dose of the Bragg peak BP1 provides the dose setting value TD1. As the thickness of the RMW 67 from the bottom surface thereof increases in the order of the regions R2, R3, ..., R11, the energy of the ion beam is attenuated at a larger rate and hence the position at which the Bragg peak is formed shifts toward the body surface of the patient. Thus, Bragg peaks BPa, BPb, BPc, etc. are formed as shown in FIG. 13. The dose of the Bragg peak BPa represents a total dose irradiated to the tumor 33 as the ion beam having passed the region Ra until the irradiation of the ion beam to the tumor 33 is completed. The dose of a Bragg peak BPc represents a total dose irradiated to the tumor 33 as the ion beam having passed the region Rc until the irradiation of the ion beam to the tumor 33 is completed. Hence, the dose of the Bragg peak BPa provides the dose setting value TDa, the dose of the Bragg peak BPb provides the dose setting value TDb, and the dose of the Bragg peak BPc provides the dose setting value TDc. In such a way, the dose setting value TDi for a certain patient 32, e.g., each of the dose setting values TD1 to TD11, is determined.

The target dose Di (i=1, 2, ..., n) is determined based on the dose setting value TDi (i=1, 2, ..., n) and the number of rotations of the RMW 67 during a period from the start of irradiation of the ion beam to the tumor 33 to the end of the irradiation. When the number of rotations of the RMW 67 during such an irradiation period is 10, for example, a relationship of Di=TDi/10 is obtained. In particular, the target dose is preferably determined using the number of rotations at which the dose can be irradiated at the maximum setting value TD1.

This second embodiment can also provide similar advantages to those obtainable with the first embodiment. In this second embodiment, the dose distribution can be more finely adjusted than in the first embodiment by changing the target dose Di (i=1, 2, ..., n) for each stepped portion (plane area). Accordingly, the dose distribution in the direction of depth can be adjusted to become uniform for a plurality of ion beams having different levels of energy (or different amounts by which a range adjuster is inserted, or different irradiation field sizes). Further, with this second embodiment, the number of rotations of the RMW can be set smaller than that in the first embodiment. Because the RMW is rotated during the irradiation for treatment in the beam delivery nozzle 15 at a position close to the patient 32, a reduction in the number of rotations contributes to improving safety. In the first embodiment, the number of the RMW's 29 to be prepared can be reduced in comparison with the related art, but several kinds of the RMW's 29 must be prepared so as to accommodate different irradiation field sizes adapted for tumors having various sizes. In contrast, this second embodiment enables one kind of the RMW 67, shown in FIG. 10, to be used for irradiation of the ion beam to tumors at different irradiation field sizes in treatment. Hence, the number of RMW's to be prepared for treatments can be remarkably reduced.

What is claimed is:

1. An ion beam delivery method for delivering, through an beam delivery nozzle, an ion beam extracted from a synchrotron, the method comprising the steps of:
   rotating a wheel installed in said beam delivery nozzle and having a plurality of stepped portions arranged in the rotating direction and having different thicknesses in an axial direction of the wheel to change energy of said ion beam passing said wheel; and
   introducing said ion beam to pass at least a part of said plurality of stepped portions of said wheel and controlling start and stop of extraction of said ion beam from said synchrotron in each of the stepped portions in said at least a part thereof which said ion beam passes, during rotation of said wheel.

2. The ion beam delivery method according to claim 1, wherein the control for the start of extraction of said ion beam from said synchrotron is performed in accordance with a rotational angle of said wheel.

3. The ion beam delivery method according to claim 1, wherein the start and stop of extraction of said ion beam from said synchrotron are performed by controlling start and stop of supply of an RF power to an RF-applying device associated with said synchrotron.

4. The ion beam delivery control method according to claim 1, wherein said start of extraction of said ion beam from said beam generator is controlled in accordance with a rotational angle of said wheel measured by a rotational angle sensor provided in said beam delivery nozzle.

5. The ion beam delivery method according to claim 1, wherein the extraction control is performed in accordance with the rotational angle of said wheel, and the extraction stop control is performed in accordance with a measured value of the dose of said ion beam passing said beam delivery nozzle.

6. The ion beam delivery method according to claim 1, wherein the extraction of said ion beam is stopped when an accumulated value of the measured dose of said ion beam passing said beam delivery nozzle has reached a target dose.

7. The ion beam delivery method according to claim 1, wherein control of performing the start and stop of extraction of said ion beam from said synchrotron includes control for start of the extraction of said ion beam in at least the part of said plurality of stepped portions and control for stop of the extraction of said ion beam, the latter control being performed in accordance with a measured dose value of said ion beam passing said beam delivery nozzle.

8. An ion beam delivery equipment for delivering a ion beam to an irradiation target, the equipment comprising:
   a synchrotron for accelerating said ion beam;
   an beam delivery nozzle including a wheel having a thickness varied in the rotating direction to change energy of said ion beam passing said wheel, and delivering said ion beam having passed said wheel to said irradiation target; and
   a controller for controlling start and stop of extraction of said ion beam from said synchrotron during rotation of said wheel,
   said wheel having a plurality of stepped portions arranged in the rotating direction and having different thicknesses in an axial direction of the wheel,
   said controller introduces said ion beam to pass at least a part of said plurality of stepped portions of said wheel and controls the start and stop of extraction of said ion beam from said synchrotron in each of the stepped portions in said at least a part thereof which said ion beam passes.

9. The ion beam delivery equipment according to claim 8, wherein said synchrotron includes an RF-applying device, and said controller controls the start and stop of extraction of said ion beam from said synchrotron and controls start and stop of supply of an RF power to said RF-applying device.

10. The ion beam delivery equipment according to claim 8, further comprising a dose monitor for detecting a dose of said ion beam passing said beam delivery nozzle,
   wherein said controller controls the extraction of said ion beam from said synchrotron in the part of said plurality of stepped portions in accordance with the rotational angle of said wheel, and stops the extraction of said ion beam from said synchrotron in one of the part of said plurality of stepped portions when a dose value detected by said dose monitor has reached a target dose for the one stepped portion.

11. The ion beam delivery equipment according to claim 8, further comprising a dose monitor for detecting a dose of said ion beam passing said beam delivery nozzle, wherein said controller stops the extraction of said ion beam from said synchrotron when an accumulated dose value detected by said dose monitor has reached a target dose.

12. The ion beam delivery equipment according to claim 8, wherein said controller controls said start of extraction of said ion beam from said synchrotron in accordance with a rotational angle of said wheel.

13. The ion beam delivery equipment according to claim 12, wherein said synchrotron includes an RF-applying device, and said controller controls the start and stop of extraction of said ion beam from said synchrotron and controls start and stop of supply of an RF power to said RF-applying device.

14. The ion beam delivery equipment according to claim 12, wherein said beam delivery nozzle includes a rotational angle sensor for detecting the rotational angle of said wheel, and said controller controls the start of extraction of said ion beam in accordance with the rotational angle measured by said rotational angle sensor.

15. The ion beam delivery equipment according to claim 14, wherein said synchrotron includes an RF-applying device, and said controller controls the start and stop of extraction of said ion beam from said synchrotron and controls start and stop of supply of an RF power to said RF-applying device.

* * * * *